Figure 1:
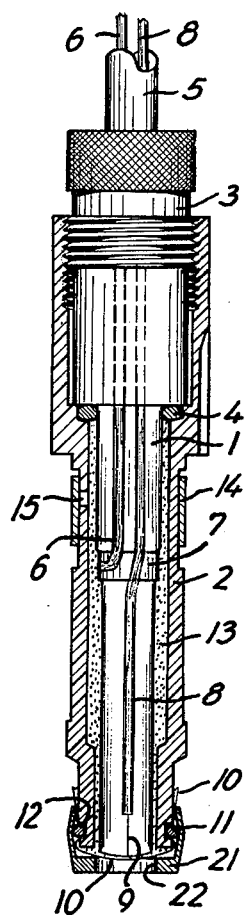

United States Patent [19]

Aas et al.

[11] 4,017,374
[45] Apr. 12, 1977

[54] ELECTROCHEMICAL MEASURING ELECTRODE

[75] Inventors: Flemming Aas, Soborg; Ole Dollerup Jensen, Herlev, both of Denmark

[73] Assignee: Radiometer A/S, Copenhagen, Denmark

[22] Filed: Sept. 23, 1974

[21] Appl. No.: 508,623

[52] U.S. Cl. .......................................... 204/195 P
[51] Int. Cl.² ................. G01N 27/30; G01N 27/46
[58] Field of Search ..................... 204/195 P, 1 T

[56] References Cited

UNITED STATES PATENTS

| 3,325,378 | 6/1967  | Greene et al. | 204/195 P X |
| 3,357,908 | 12/1967 | Riseman et al. | 204/195 P |
| 3,406,109 | 10/1968 | Molloy | 204/195 P |
| 3,418,231 | 12/1968 | Haddad | 204/195 P |
| 3,454,485 | 7/1969  | Hauk et al. | 204/195 P |
| 3,510,421 | 5/1970  | Gealt | 204/195 P |
| 3,655,546 | 4/1972  | Marovich et al. | 204/195 P |
| 3,718,566 | 2/1973  | Krebs | 204/195 P |
| 3,758,398 | 9/1973  | Doniguian | 204/195 P |
| 3,875,037 | 4/1975  | Krull | 204/195 P |

*Primary Examiner*—G. L. Kaplan
*Attorney, Agent, or Firm*—Stevens, Davis, Miller & Mosher

[57] ABSTRACT

Electrochemical measuring electrodes often have a thin foil-shaped membrane, e.g. made of a plastic foil, which is arranged at one end of a cylindrical portion of the electrode and maintained in position by means of a resilient ring-shaped member, e.g. an O-ring, which presses the folded-over edge portion of the membrane against the outside of the cylindrical portion. It is now suggested to guide the ring-shaped holding member in such a way on the cylindrical portion that it protrudes beyond the membrane and thereof. The guiding may be provided by means of a circumferential groove in the cylindrical portion near the membrane end thereof.

1 Claim, 4 Drawing Figures

ELECTROCHEMICAL MEASURING ELECTRODE

The present invention relates to electrochemical measuring electrodes. Such electrodes are often provided with a thin foil-shaped membrane, e.g. of a plastic foil, as the active element. This membrane is supported on one end of a substantially cylindrical portion of the measuring electrode and is maintained in position by means of a resilient ring-shaped holding member, e.g. an O-ring, which is inserted over the membrane end of the cylindrical portion and presses the folded-over edge portion of the membrane against the outside of the cylindrical portion. The position of the holding member on the cylindrical portion may be determined by means of a circumferential groove in said portion. When an electrode of this type is to be used in connection with a measuring chamber, it is positioned so in relation to the chamber that the membrane forms part of the wall of the measuring chamber. In order to obtain a sealing in relation to the walls of the measuring chamber the membrane end of the cylindrical portion is provided with a resilient cap having an aperture opposite the central part of the membrane and covering, at least partially, the folded-over edge portion of the membrane and the holding member.

This known electrode has a number of draw-backs resulting from the use of the cap. This cap is an additional element which has to be mounted when assembling the electrode, and behind the cap there are a number of small spaces in which residues of the samples may be left, so that contamination occurs.

Accordingly it is an object of the present invention to provide an electrochemical measuring electrode which is of a simple construction and which can easily be assembled and mounted in connection with the measuring chamber.

It is a further object of the present invention to provide an electrochemical measuring electrode in which substantially no residues of the samples are left.

These and further objects of the present invention are attained by the provision of guiding means on the cylindrical portion, by which means the holding member is maintained in such a position that it protrudes beyond the end surface of the cylindrical portion. Hereby is obtained that one member, the resilient holding member, carries out two functions, namely maintaining the membrane in position on the cylindrical portion and providing sealing of the electrode against the walls of the measuring chamber whereby the cap can be completely dispensed with. Furthermore there are now practically no spaces where residues of the samples can be left.

The invention will now be described more in detail with reference to the accompanying schematical drawing in which FIG. 1 shows a longitudinal section through a known electrochemical measuring electrode to which the present invention may be applied, FIG. 2 on a larger scale the membrane end of the electrode according to FIG. 1 inserted into a measuring chamber, FIG. 3 a first embodiment of the electrode according to the invention in a view responding to FIG. 2 and FIG. 4 another embodiment of the electrode according to the invention.

Figure 2:
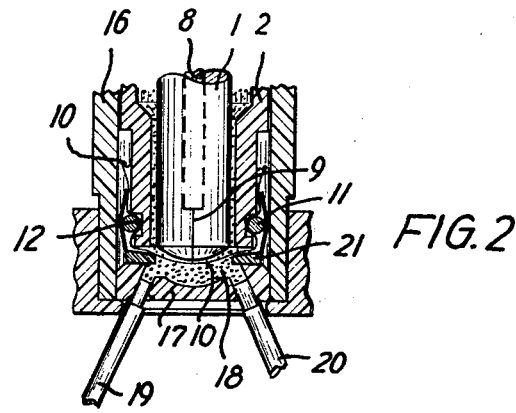

The electrode shown in FIGS. 1 and 2 includes an electrode body 1 and an electrode jacket 2 into which the electrode body is inserted. A nut 3 is screwed into the jacket 2, thereby pressing the electrode body 1 against a sealing ring 4.

A two-wire conductor 5 passes through the nut 3 to the interior of the electrode body 1. One 6 of the wires is connected to a silver/silver chloride electrode element 7 in the electrode body 1, which is otherwise made from an electrically insulating material, e.g. glass.

The other wire 8 is near the lower end of the electrode body 1 connected to a thin platinum wire 9 which ends on the lower surface of the body 1. The lower end of the jacket 2, which is substantially cylindrical, is closed by means of a thin membrane 10 stretched over the end surface of the jacket 2 and the adjacent end surface of the body 1 and held in position by a holding means in the form of an elastic O-ring 11 seated in an annular groove 12.

An electrolytic solution 13 is trapped between the body 1, the jacket 2 and the membrane 10. A rubber band 14 closes a small hole 15 in the jacket through which any surplus of electrolyte can escape during the mounting of the electrode.

In FIG. 2 the lower end of the electrode according to FIG. 1 is inserted into a measuring chamber having a cylindrical side wall 16 and a button wall 17. The sample to be examined by the electrode is introduced into the measuring cavity 18 through an inlet tube 19 and is expelled through an outlet tube 20. The membrane 10 constitutes one of the walls of the measuring cavity 18 and in order to obtain a tightening between the electrode and the walls of the measuring chamber a cap 21 is provided on the membrane end of the cylindrical part of the jacket 2, see also FIG. 1. The cap 21, which is of a resilient material, has a central aperture 22 through which a membrane 10 will come into contact with the sample in the measuring cavity 18.

The electrode described with reference to FIGS. 1 and 2 may be designed to measure the partial pressure of oxygen in gas mixtures, solutions or on moist surfaces. In that case the cathode 9 may be a platinum wire having a diameter of $20\mu$ and the membrane 10 may be a plastic foil, e.g. a polypropylene foil, of a thickness of about $20\mu$. The electrolyte may then be a phosphate buffer to which some potassium chloride has been added. A polarizing voltage of e.g. 650 mV is applied between the cathode 22 and the anode 7. When a sample, e.g. blood, is introduced into the measuring cavity 18, oxygen will diffuse through the membrane and will be reduced at the platinum electrode according to the relation:

$$O_2 + 2H^+ + 2e^- \rightarrow H_2O_2.$$

Hereby an electric current will be produced, which is proportional to the oxygen pressure and which can be measured by a current measuring instrument.

Figure 3:
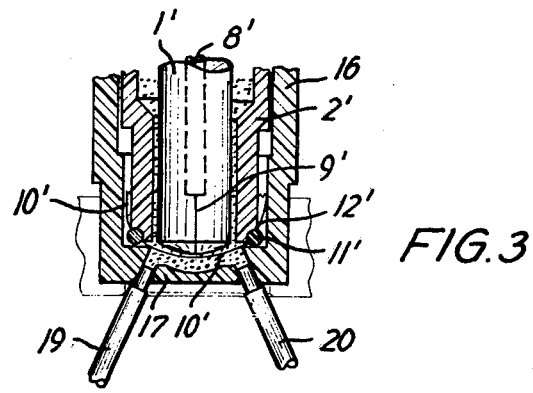
Figure 4:
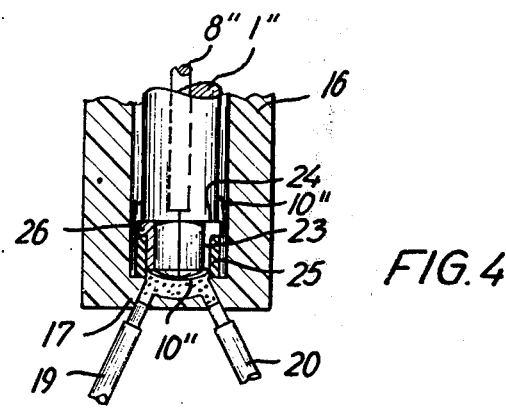

The electrode, to which the present invention, as exampled by FIGS. 3 and 4, may be applied, can be of this type, but can also be designed for measuring the pressure of other gasses, e.g. carbon dioxide, or it may be of a different construction in other respects, the features important for the invention being the presence of a cylindrical portion on the electrode, e.g. on the electrode jacket, on one end of which a foil-shaped membrane is mounted and maintained in position by means of a resilient ring-shaped holding member.

In the embodiment according to FIG. 3 an electrode comprising an electrode body 1' and an electrode jacket 2' is inserted into the measuring chamber having the cylindrical side wall 16 and the bottom wall 17. The membrane 10' is held in position by means of a resilient O-ring 11' seated in a circumferential groove 12', which is so positioned in relation to the cross section of the O-ring that this ring extends beyond the end face of the jacket 2'.

In this case the ring 11' fulfills a double function. It serves to maintain the membrane 10' in position on the cylindrical portion of the jacket 2' as does the ring 11 in the device according to FIGS. 1 and 2, and it provides sealing of the electrode against the measuring chamber, said sealing being provided by the cap 21 in the device according to FIGS. 1 and 2. This has the advantage that the device consists of fewer parts and, what is probably more important, only one element in addition to the membrane has to be arranged on the electrode when it is being prepared for use. Furthermore in the known device according to FIGS. 1 and 2 there is a risk that the arrangement of the cap 21 on the cylindrical portion may disturb the previous correct mounting of the membrane. Finally the cap provides a number of small narrow spaces where residues of the sample may deposit and from which they can only with difficulty be removed. In the embodiment according to FIG. 3 the risk of such deposits is substantially reduced.

In FIG. 4 the electrode 1" has near its lower end a cylindrical part 23 of a electrically insulating material, e.g. a plastic material. This cylindrical part 23 rests against a shoulder 24 on the electrode body 1". A membrane 10" is provided on the end surface of the cylindrical part 23 and is maintained in position by means of a holding member in the form of a short cylinder or tube 25 of a resilient material. One end of the tube 25 rests against a flange 26 on the cylindrical part 23 and the other end of the tube 25 extends beyond the end surface of the cylindrical part 23. When the electrode body 1" and the parts mounted thereon are inserted into the measuring chamber, the tube 25 will, in addition to maintaining the membrane in position, provide the required sealing against the walls of the measuring chamber.

The invention is in no way limited to the embodiments described with reference to FIGS. 3 and 4 of the drawing, but can be varied within the scopes of the appended claims.

What is claimed is:

1. An arrangement for carrying out electrochemical measurements on samples, comprising
   a measuring chamber having walls surrounding a measuring cavity, inlet and outlet means for introducing the samples into and expelling them from the measuring cavity, and a hole in the walls leading to the measuring cavity, in combination with
   an electrochemical measuring electrode including a substantially cylindrical portion, a thin foil-shaped membrane arranged over an end face of the cylindrical portion and folded along the adjacent cylindrical outer wall of the cylindrical portion, a resilient O-ring inserted over the folded-over part of the membrane and a circumferential groove in the cylindrical portion at the transition from the cylindrical outer wall to the end face thereof, the groove being of such dimension in relation to the O-ring and so positioned that the O-ring, when seated in the groove, will be maintained therein by its elastic force and extends beyond the end face of the cylindrical portion, whereby, when the electrode is placed so in relation to the measuring chamber that the membrane covers the hole in the walls of the measuring chamber, the O-ring will in addition to maintaining the membrane in position on the cylindrical portion, provide a sealing of the membrane against the walls of the measuring chamber.

* * * * *